United States Patent [19]

Annis

[11] Patent Number: 4,899,283
[45] Date of Patent: Feb. 6, 1990

[54] TOMOGRAPHIC APPARATUS INCLUDING MEANS TO ILLUMINATE THE BOUNDED FIELD OF VIEW FROM A PLURALITY OF DIRECTIONS

[75] Inventor: Martin Annis, Cambridge, Mass.
[73] Assignee: American Science and Engineering, Inc., Cambridge, Mass.
[21] Appl. No.: 123,630
[22] Filed: Nov. 23, 1987
[51] Int. Cl.$^4$ ............................................. G06F 15/38
[52] U.S. Cl. ............................... 364/413.15; 378/146; 364/413.14
[58] Field of Search ...................... 364/413.14, 413.19, 364/413.15; 378/146, 147

[56] References Cited
U.S. PATENT DOCUMENTS
4,096,389 6/1978 Ashe et al. ................... 378/147 X
4,260,898 4/1981 Annis .............................. 378/146
4,349,739 9/1982 Annis .............................. 378/99
4,366,576 12/1982 Annis .............................. 378/146
4,414,682 11/1953 Annis .............................. 378/146
4,503,332 3/1985 Annis .......................... 378/146 X Primary Examiner—Jerry Smith
Assistant Examiner—Gail O. Hayes
Attorney, Agent, or Firm—Pollock, Vande Sande & Priddy

[57] ABSTRACT

Tomographic imaging with the aid of a line collimator is improved by providing for the illumination of a given linear element of the selected slice from a plurality of different directions. The line images resulting from illumination from different directions are then processed so as to minimize or eliminate spurious features of the image which result from portions of the object not lying along the slice but closer to the source of penetrating radiant energy than the slice plane.

16 Claims, 8 Drawing Sheets

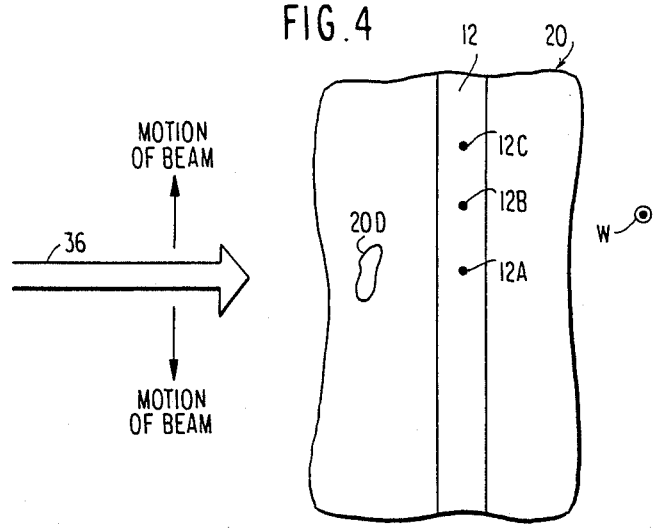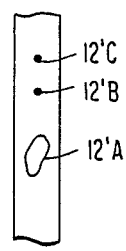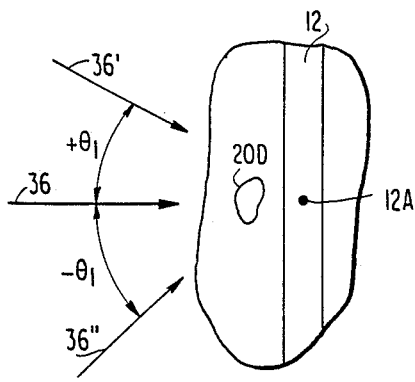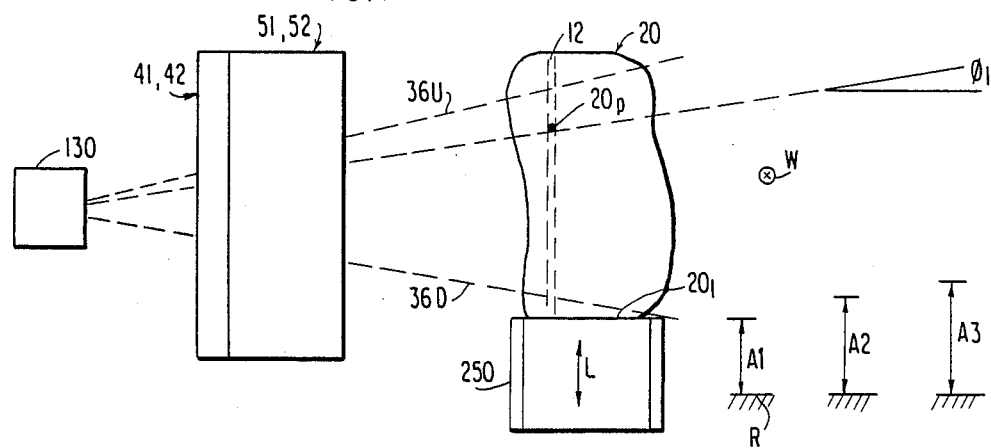

| PASS | ANGLE | SIGNAL | | | | | | |
|---|---|---|---|---|---|---|---|---|
| 1 | 90° | $LI_{11}$ | $LI_{12}$ | $LI_{13}$ | --- | --- | --- | $LI_{17}$ |
| 2 | 90°+$\theta_1$ | $LI_{21}$ | $LI_{22}$ | $LI_{23}$ | --- | --- | --- | $LI_{27}$ |
| n | 90°−$\theta_2$ | $LI_{n1}$ | $LI_{n2}$ | $LI_{n3}$ | | | | $LI_{n7}$ |

| PASS | HEIGHT | SIGNAL | | | | | | |
|---|---|---|---|---|---|---|---|---|
| 1 | A1 | $LI_{11}$ | $LI_{12}$ | $LI_{13}$ | --- | --- | --- | $LI_{17}$ |
| 2 | A2 | $LI_{21}$ | $LI_{22}$ | $LI_{23}$ | --- | --- | --- | $LI_{27}$ |
| n | An | $LI_{n1}$ | $LI_{n2}$ | $LI_{n3}$ | | | | $LI_{n7}$ |

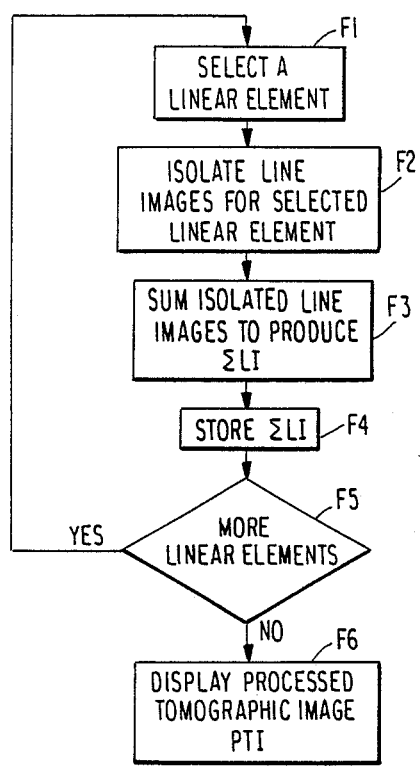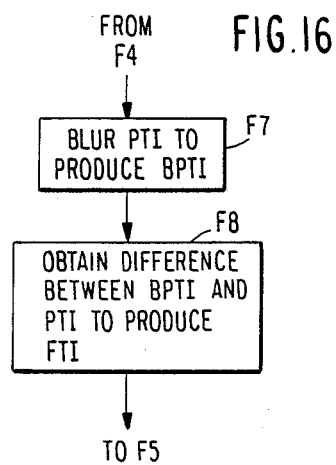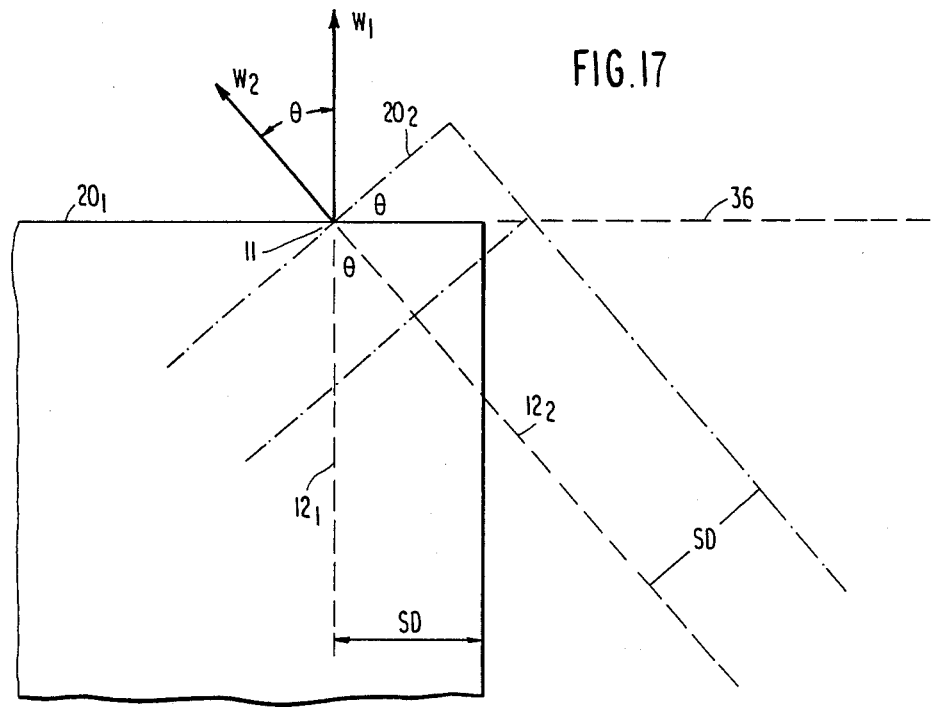

TOMOGRAPHIC APPARATUS INCLUDING MEANS TO ILLUMINATE THE BOUNDED FIELD OF VIEW FROM A PLURALITY OF DIRECTIONS

TECHNICAL FIELD

This invention relates to the production of tomographic images by using penetrating radiation.

CROSS-REFERENCE TO RELATED APPLICATION

The present application is an improvement on the invention disclosed and claimed in the copending application entitled "Method and Apparatus for Producing Tomographic Images", U.S. patent application Ser. No. 888,019, in the name of the present inventor and assigned to the assignee of this application. The subject matter of S.N. 888,019 is incorporated herein by this reference.

BACKGROUND ART

The application cross-referenced above discloses and claims a method and apparatus for producing tomographic images. The images produced by the device described in the cross-referenced application can be considered to be the product of five terms, of which three are variable. Of the variable terms, one term is a function of the attenuation of the illuminating beam along its path from the source to the slice, another term is the proportion of incident energy which is scattered by the illuminated volume element of the object within the slice and the third term is a function of the attenuation of the scattered energy on its way out of the object being imaged. The two constant terms are the incident flux or illuminating radiation and geometrical factors dictated by the solid angle subtended by the detectors and the transmission ratio of the line collimator. An ideal image is formed when the only variable is the fraction of the illuminating energy which is scattered by the volume element being imaged. The fact that the image is also a function of the attenuation of the beam on its way in means that the resulting image is in a sense an image of the "slice" as seen through a filter (consisting of the overlying material) whose density is determined by the overlying material which is in line with the illuminating beam. Because the density of the overlying material can vary, those variations will show up as (unwanted) modulation in the resulting image, which are not the result of actual variations due to x-ray scattering within the "slice".

It is a purpose of this invention to eliminate or minimize this variable.

As described in the copending application, tomographic imaging in accordance with that invention is achieved by generating a pencil beam of illuminating radiation and sweeping that pencil beam over a line in space to define a sweep plane, locating the object to be imaged so that the pencil beam intersects the object and the selected slice, locating a line collimator whose line of focus coincides with that particular linear element of the selected slice which is illuminated by the sweeping pencil beam, e.g. locating the line collimator so that its field of view intersects the sweep plane in a bounded line which lies in the selected slice. A radiation detector is provided to respond to radiant energy passing the line collimator. For reasons more particularly described in the copending application, the radiant energy detector will "see" a sequence of signals describing the radiation response of that linear portion of the selected slice illuminated by the pencil beam. We can refer to this sequence as a line image of a linear element of the slice. The illuminated linear element or portion of the selected slice is the portion of the slice along the bounded line. By providing proper motion of the object relative to the source/detector/line collimator, we can provide for the bounded line to trace out the selected slice so that as a function of time, the response of the detector will describe the selected slice. Thus the image generated in the structure of the copending application is merely a concatenation of signal sequences (one or more sequence per line image) as described above, at least one sequence for each different instance of the bounded line in the selected slice.

It is an object of the present invention to reduce or minimize the modulation or variation of the tomographic image caused by variations in that portion of the object lying between the selected slice and the source of the pencil beam. As described in the copending application, density variations in this portion of the object will "modulate" the resulting tomographic image. Thus it is an object of the invention to reduce or minimize this "modulation" of the resulting tomographic image.

SUMMARY OF THE INVENTION

The method and apparatus described in the copending application is changed in accordance with this invention in the following fashion. Rather than illuminating the bounded line (the intersection of the field of view of the line collimator and the sweep plane) from a fixed direction, that intersection or bounded line is illuminated from a plurality of directions.

The radiation detector will produce a signal sequence for each different direction of illumination. Each signal sequence can be considered a "line image" of a particular linear element of the selected slice, and of course each line image will be of the identical linear element of the selected slice, although taken from a different direction. So instead of having one or more signal sequences LI for each linear element taken from a fixed direction (as in the referenced application), we have line images or signal sequences $LI_1, LI_2, LI_3, \ldots LI_n$, of a single linear element of the slice, taken from different directions.

Once a line image is generated by illumination from different directions, the line image (or the signal sequences) for the object illuminated from the different directions are summed. That is, for each linear element of the slice we produce $$\sum_{i=1}^{i=n} LI_i$$

$= LI_1 + LI_2 + LI_3 + \ldots LI_n$, where $\Sigma LI_i$ is a sum line image ($\Sigma LI$). In the sum line image the effect of features of the object between the source of the pencil beam and the bounded line (but not on the bounded line) will become blurred. In one embodiment of the invention the tomographic image is formed by concatenating a set of the sum signal sequences, one (or more) sum signal sequence for each linear element in the slice. The result of this processing is a processed tomographic image of the slice being examined.

However, in another embodiment the processed tomographic image is high frequency filtered (some-times called blurred mask subtraction) to remove the blurred overlying modulation. This procedure is particularly effective because the overlying modulation is already blurred. In this procedure the processed tomographic image is further blurred by replacing each pixel of the image by an average of, say, 15 pixels (usually called the "kernel") surrounding the chosen pixel resulting in a very blurred image. This very blurred image is then subtracted from the processed tomographic image which results in substantial removal of the blurred background in the original image. The size of the "kernel" is chosen (for example, experimentally) to optimize the removal of the blurred portion of the image.

A tomographic image produced as described in the copending application may exhibit the modulation effects of density variations between the pencil beam and the selected slice. By summing line images and processing as described, the "modulation" caused by density variations in the object between the selected slice and the pencil beam can be minimized or eliminated.

In order to implement the processing which has just been described, it is essential to be able to illuminate any selected linear element of the slice from different directions. This illumination from different directions requires us to provide some relative motion between the object in which the selected slice exists, and the imaging apparatus. The copending application already describes one form of relative motion between the object and the imaging apparatus. The copending application describes that with the object in any given position (which results in illumination of the selected linear element) the signal sequence produced by the detector describes the radiation response of that linear element, e.g. the linear element which coincides with the bounded line which is the focal line of the line collimator. The slice however is made up of a number of such linear elements and thus in order to produce an image of the slice we must move the object so that the bounded line coincides with each of the linear elements making up the selected slice. One form of that motion is a translating motion of the object in a direction which is perpendicular to the longitudinal extent of the bounded line; this motion will produce an image of a slice which is substantially planar (other forms of motion for different slice geometries are also described in the copending application). As the object moves relative to the imaging apparatus, each linear element is illuminated from the same direction. Thus in order to implement the present invention we must ensure that each linear element is illuminated from many directions. This can be implemented in a number of different ways.

If we are imaging a selected slice which is substantially planar, then as already described the object will be moved relative to the imaging apparatus in a direction generally perpendicular to the longitudinal extent of the bounded line. The repositioning of the object so as to achieve illumination of each linear element from many directions can be achieved by:

(1) interrupting the relative motion of the object past the imaging apparatus for each different linear element, and while the motion of the object is interrupted, repositioning the object by rotating it about an axis coincident with the bounded line so as to achieve several different angular orientations of the object (and the selected slice) with respect to the imaging apparatus. For each different such angular orientation a line image is detected and recorded, and processed as already described. While this will clearly achieve the purpose of illuminating each linear element in the selected slice from many different directions, it has the disadvantage of interrupting the longitudinal movement of the object which destroys the smooth sampling of the detector output, and it requires a mechanical apparatus for moving the object with two distinctly different types of motion, e.g. the linear motion to translate the object longitudinally and the rotary motion which must rotate the object about a precise axis. This technique also has the disadvantage of impacting the time required to accurately reposition the object.

(2) A more practical alternative is to repeatedly translate the object from an initial position past the imaging apparatus. In one such translation the object is positioned exactly as is described in the copending application. This operation then will produce a line image for each different linear element in the selected slice, exactly as described in the copending application. Thereafter the object is returned to or near the initial position and again translated past the imaging apparatus. Before the second translation the object is reoriented relative to the imaging apparatus, and it is translated past the imaging apparatus in a direction which is angularly offset from the direction in which the object was translated on the first pass. The object is repositioned so that, considering the angle at which it is translated relative to the imaging apparatus and the spacing between the object and the imaging apparatus, the imaging beam always intersects the selected slice the same distance from the collimator as it did on the first pass. Of course that same distance is the focal length of the collimator. On this second pass, a signal sequence is recorded for each linear element of the slice, exactly as it was on the first pass. On the second pass, however, since the object's translation is at an angle to the direction in which it was translated on the first pass, the angle at which the selected slice is illuminated is different from the angle at which it was illuminated on the first pass. This provides for a line image of each linear element from a direction different from that in which it was illuminated on the first pass. The object is again returned to or near the initial position and again translated past the imaging apparatus on a third occasion. The angle at which the object is translated past the imaging apparatus differs from the angle in which it was translated on the first two passes. Before the translation the object is repositioned so that the illuminating beam intersects the selected slice at the same fixed distance from the collimator as it did on the first two passes. A further signal sequence is recorded for each linear element of the selected slice. This third pass again provides for a line image of each linear element of the selected slice which is illuminated from a direction different from the directions in which the same line image was illuminated on the first two passes. This procedure can be repeated a number of times. The result of recording all the line images will result in a plurality of line images for each linear element of the selected slice. The line images for any linear element of the selected slice are then processed as already described.

(3) The foregoing two techniques which have been described for the relative motion between the object and the imaging apparatus provide two different techniques for in effect rotating the illumination direction for each of a plurality of line images by rotating the object being illuminated about an axis coincident with the bounded line. However, that is not an essential component of the invention for we can obtain illumination from different directions by translating the object in a direction parallel to the bounded line. This translation can also be performed in two different ways, analogous to the two different ways in which rotation can be implemented. That is, (a) the translation of the object past the imaging apparatus in the direction described in the copending application is interrupted. During a single interruption the object may be translated, from a base position, in a direction along the bounded line, or parallel to that direction, so the object achieves several different positions in elevation relative to the imaging apparatus. At each of these different positions a line image is recorded. The object is then returned to its base position and moved in translation (generally perpendicular to the bounded line) and after a given amount of this motion, the motion is again interrupted and the foregoing process is repeated. This arrangement has the same practical difficulties as has already been described with respect to interrupting translation to provide for rotation.

(b) Thus, the preferred technique for translation parallel to the bounded line is to translate the object past the imaging apparatus in a direction generally perpendicular to the bounded line so that the entire slice is illuminated, and recording line images for each different linear element of the selected slice. The object is then repositioned, e.g. returned to or near its starting position, and translated along or parallel to the bounded line to achieve an elevated or depressed position relative to the position it had achieved prior to the first translation. The object is then translated past the imaging apparatus in this elevated or depressed position and a line image is recorded for each linear element of the selected slice. This procedure may be repeated a number of times at different elevations or depressions relative to the base position. The different line images for a given linear element are then processed as will be described.

These different motions, all of which are relative motion between the object and the imaging apparatus, is usually implemented by moving the object and maintaining the imaging apparatus stationary. In some cases, however, where the object being imaged is as large or even larger than the imaging apparatus, it may be advisable to provide the relative motion by keeping the object stationary and moving the imaging apparatus. Assuming however that the relative motion is produced by moving the object past a stationary imaging apparatus, then the invention can be implemented by using first a conventional conveyor for providing the translatory motion of the object generally perpendicular to the bounded line. In those embodiments of the invention in which the different directions of illumination are achieved by rotating the object about the bounded line, the conveyor itself is mounted on a turntable. Thus the conveyor is operated on a first pass to move the object past the imaging apparatus with the turntable at a base or reference position. Once the object has been translated sufficiently far to illuminate all of the selected slice, the conveyor motion is terminated, the object is returned to or near its initial position, the conveyor is rotated from the base or reference orientation, the object properly positioned on the conveyor and the conveyor is again initiated to translate the object past the imaging apparatus. The combined result of rotating the conveyor and repositioning the object achieves the goal of ensuring that each linear element of the selected slice remains the desired fixed distance from the line collimator. For embodiments of the invention wherein the different illumination directions are achieved by translating the object in a direction parallel to the bounded line, the conveyor is not mounted on a turntable, but rather the conveyor is mounted on an elevator and the procedure as already described is repeated except that instead of rotating the conveyor, the conveyor is elevated or depressed relative to the imaging apparatus. It should be apparent that, in cases where the relative motion is achieved by moving the imaging apparatus relative to a stationary object, that the conveyor is used to provide translatory motion of the imaging apparatus and the conveyor can be mounted on a turntable or elevator as has already been described. It is usually preferable to arrange the successive views of the slice so that overlying material is blurred strongly. In some cases, the overlying material may be in the form of a line. In these cases it is better to achieve successive views perpendicular to this line.

Accordingly, in one embodiment the invention provides a device useful in producing a tomographic image of a selected slice of an object to be examined, said device comprising:

a source of penetrating radiation, sweep means for forming energy from said source into a pencil beam and for repeatedly sweeping said pencil beam over a line in space to define a sweep plane, first means for supporting an object to be examined so that said pencil beam intersects said object along a path passing through said object and said selected slice, line collimating means for filtering radiation scattered by said object, said line collimating means having a field of view which intersects said sweep plane in a bounded line so that said line collimating means passes only radiation scattered by elementary volumes of said object lying along said bounded line, positioning means for repositioning said object so that a linear segment of said selected slice of said object is illuminated by said sweeping pencil beam from a plurality of different directions, radiation detector means responsive to radiation passed by said line collimating means for generating at least a different signal sequence for each of said different directions of illumination of said linear segment of said selected slice of said object, and processing means responsive to said signal sequences for producing a line image component of a tomographic image.

In another embodiment the invention provides a method useful in generating a tomographic image of a selected slice of an object by generating a line image of said selected slice comprising the steps of:

providing a source of penetrating radiation, forming a pencil beam from energy emitted by said source and repeatedly sweeping said pencil beam over a line in space, supporting an object to be examined so that said pencil beam intersects said object along a path passing through said object and said selected slice, positioning said object so that a given linear segment of said selected slice of said object is illuminated from a plurality of different directions relative to said sweeping pencil beam, filtering radiation scattered by said object to pass only radiation scattered by elementary volumes of said object lying along a line defined by a succession of intersections between said path and said selected slice by interposing a radiation absorbing structure with plural, substantially planar, radiation transmitting channels between said object and a radiation detector, detecting radiation passed by said filtering step to form a different signal sequence for each different direction from which said linear segment of said selected slice of said object is illuminated, and processing said signal sequences to form a line image component of a tomographic image.

BRIEF DESCRIPTION OF THE DRAWINGS

The invention will now be further described in the following portions of this specification when taken in conjunction with the attached drawings in which like reference characters identify identical apparatus and in which:

FIG. 4 is a section, in elevation, useful in explaining the principles of the present invention;

FIG. 5 schematically illustrates a portion of a tomographic image which can be improved in accordance with the present invention;

FIG. 6 is a plan view useful in explaining how illumination from different directions can be used to improve imaging in accordance with the first embodiment of the present invention;

FIG. 7 is an elevation view useful in explaining a second embodiment of the invention;

FIG. 15 is a flow diagram of data processing in accordance with the invention;

FIG. 16 is further, optional processing in accordance with the invention;

FIG. 17 is useful in explaining the relationship of line images as the object is rotated.

DETAILED DESCRIPTION OF PREFERRED EMBODIMENTS

Figure 1:
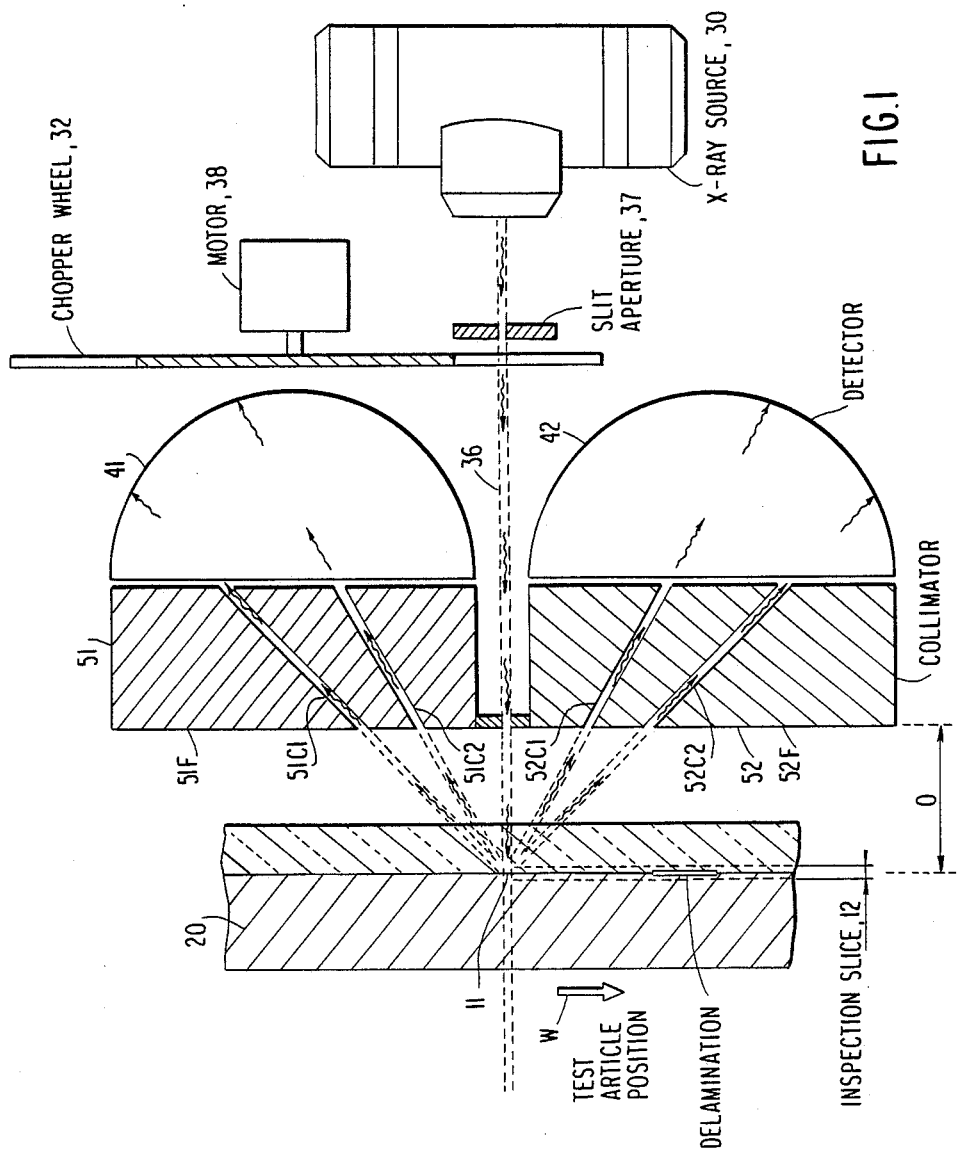
FIGS. 1, 2 and 3 are similar plan views of the imaging apparatus employed in the present invention showing illumination of a given linear segment of a slice of the object 20 from three different directions in accordance with a first embodiment of the present invention.

FIG. 1 is a cross-section (in plan) of the inventive apparatus illustrating the source of the pencil beam as including the x-ray source 30, the chopper wheel 32, motor 38, slit aperture 37. As seen in FIG. 1 the pencil beam 36 illuminates the object 20 being imaged. As the motor 38 rotates the chopper wheel 32, the pencil beam sweeps in the plane 36 (perpendicular to the plane of the illustration of FIG. 1) to sweep out a bounded line which is represented in FIG. 1 by the point 11. The object 20, illuminated as it is along the line 36, can scatter energy from any volume element of the object lying along the path of illumination. However, the line collimator comprising line collimator elements 51 and 52 is designed to pass only that energy scattered from elementary volumes of the object 20 lying along the line of focus represented by point 11. Scattered energy passed by the collimator elements 51 and 52 is detected by the radiation detector elements 41 and 42. The signals produced by the detector elements 41 and 42 are summed to produce, at any instant in time, a single signal representing the radiation response of the particular elementary volume of the object 20 which lies along the line of focus of the line collimator elements 51 and 52 and which is illuminated by the pencil beam 36. Thus with the object fixed in the position of FIG. 1, as the pencil beam 36 sweeps the bounded line the output of the detecting elements 41, 42 is a sequence of signals which can be considered a line image LI of the illuminated linear element of the slice. As described in the copending application, the object 20 being illuminated is moved in the direction of the arrow W relative to the imaging apparatus. At each position of the object 20 relative to the x-ray source 30, the pencil beam illuminates a different linear element of the object within the slice 12. The signals produced by the detector elements 41 and 42 corresponds to a line image of that particular linear element of the slice 12. As the object moves relative to the imaging apparatus in the direction W a sequence of such line images are produced, processed, stored and concatenated to produce an image of the selected slice 12. That is, if the slice has five linear elements (elements 1-5) the device described in the copending application produces a line image for each, e.g. $LI_1$-$LI_5$ (of course typical slices have many more line images than five).

In accordance with the present invention, the positional relationship of the object 20 relative to the source/detector/line collimator is changed so that each linear element of the slice 12 is illuminated by the pencil beam from a plurality of different directions and a different signal sequence is derived for each different direction of illumination. One such positional relationship or illumination direction is as is illustrated in FIG. 1; this may be referred to as a reference position only because it is the position described in the copending application. The signal sequence produced by the radiation detector elements 41, 42 in the position may be referred to as a reference line image.

Figure 2:
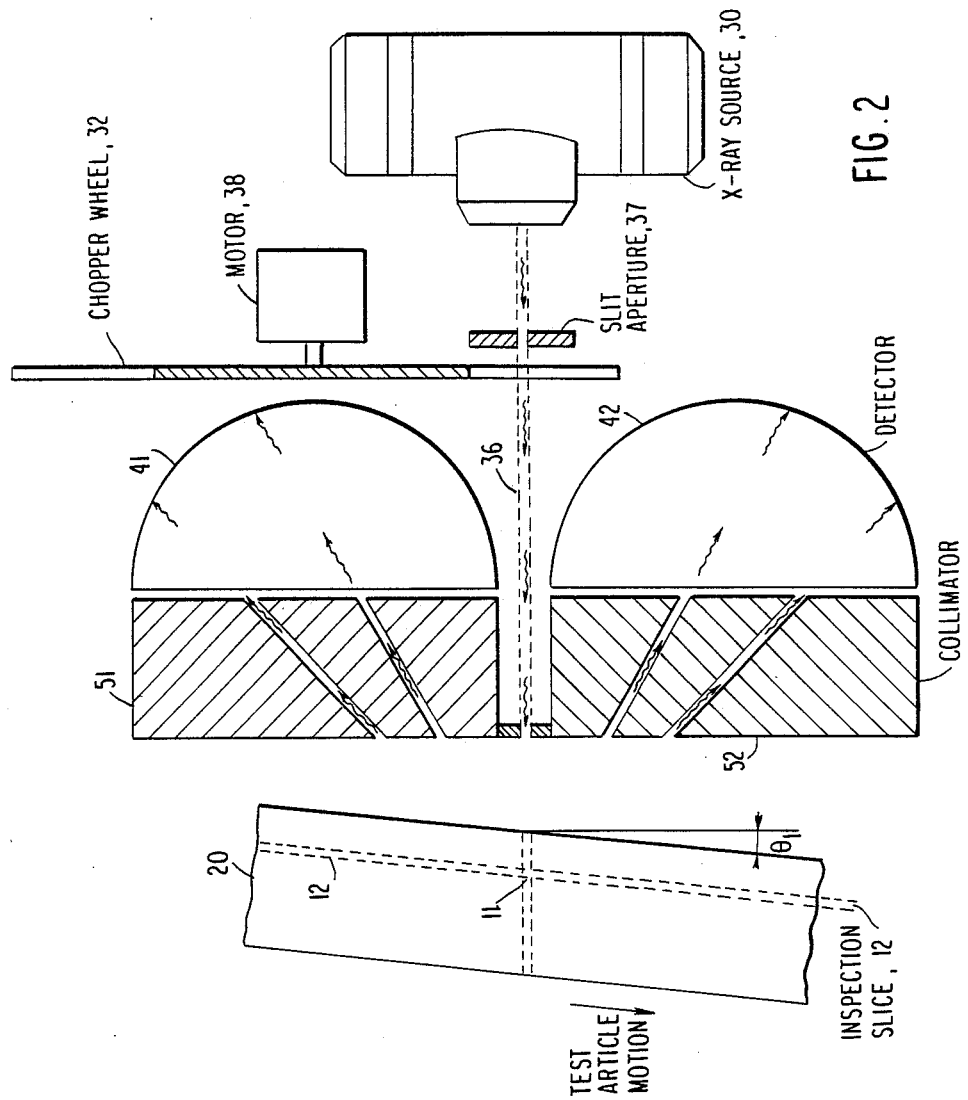
Figure 3:
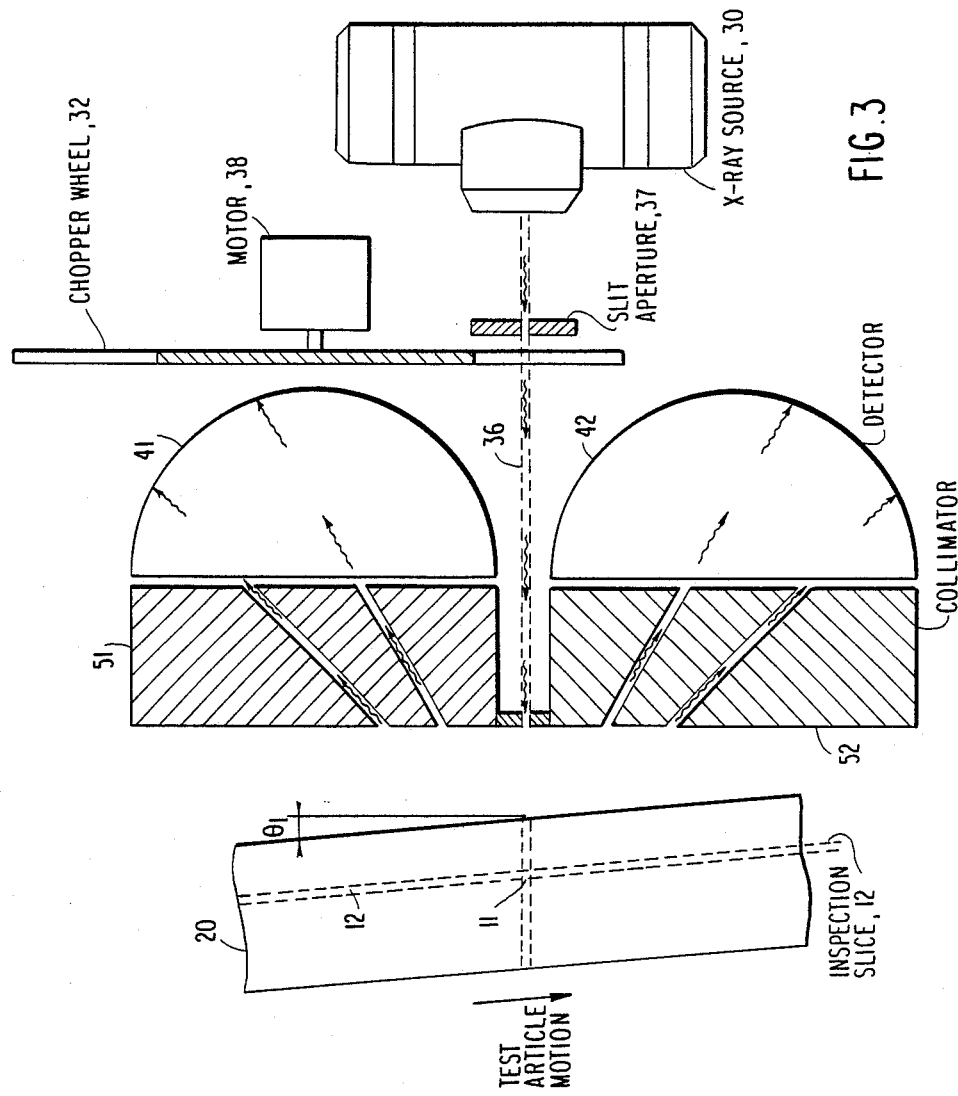

As shown in FIG. 2, the object is in the same positional relationship to the source/detector/line collimator as is shown in FIG. 1 (that is, the same linear segment of the slice 12 is illuminated in both FIG. 1 and FIG. 2) except that the object has been rotated through an angle $\Theta_1$ about an axis which is colinear with the bounded line (represented in FIG. 2 by the point 11). With the object in this position relative to the source/detector/line collimator, a different or second signal sequence is generated and stored. The position of the object 20 relative to the source/detector/line collimator is now varied from that shown in FIGS. 1 and 2 to that shown in FIG. 3. As shown in FIG. 3 the object 20 is rotated through an angle $\Theta_1$ in the opposite direction from that shown in FIG. 2 with respect to the reference position (FIG. 1). At this position of the object 20 relative to the source/detector/line collimator, the same linear element of the slice 12 is again illuminated at a still further different direction. A further signal sequence is derived. While the foregoing describes deriving three signal sequences with the object in three different positions wherein the same linear segment is illuminated, preferably more than the three illumination directions already illustrated are used. The only requirement is that the linear element of the selected slice be illuminated from different directions. There are plural line images, each of the same linear element but illuminated from different directions, e.g. for an arbitrary linear element we produce line images $LI_1^2$, $LI_2^2$, $LI_3^3$, ... $LI_n^2$, where the subscript refers to illumination directions 1 to n and the superscript identifies the common linear segment of the slice.

FIG. 4 is a cross-section (in elevation and thus different from the section of FIGS. 1-3) illustrating the illuminating beam 36 and a section of the object 20 being imaged. The reference character 12 identifies the slice being imaged. In the view of FIG. 4 the motion of the illuminating beam 36 is within the plane of the illustration and hence the motion of the object in the direction W, is perpendicular to the plane of illustration. For purposes of description, we have represented three distinct elements within the selected slice 12, e.g. elements $12_A$ through $12_C$. We have also illustrated in FIG. 4 a density variation by the region $20_D$ located between the source of illumination and the selected slice. The region $20_D$ is a high density region which is located within the object 20, between the plane of the selected slice 12 and the source of the pencil beam 30. The high density region $20_D$ is located between the feature $12_A$ in the selected slice 12 and the source of the pencil beam 30, although it is not located between the source of the pencil beam 30 and the features $12_B$ and $12_C$. FIG. 5 is an illustration of the resulting tomographic image of this particular line element of the object 20 that would be produced without employing principles of the present invention. As shown in FIG. 5, the tomographic image will properly image the features $12_C$ (as feature $12'_C$) and $12_B$ (as feature $12'_B$). However the feature $12_A$ will not be properly illustrated in that its effect may be "hidden" or degraded by the attenuation interposed to the pencil beam 36 by the high density region $20_D$ to produce image element $12'_A$.

In order to minimize or eliminate the undesired image or image modulation produced by the high density element $20_D$, the object 20 is illuminated from directions other than the direction 36 shown in FIG. 4. FIG. 6 is a section (in plan) similar to FIGS. 1-3, showing the different directions 36, 36', 36" from which the object 20 may be illuminated. Each of the directions 36' and 36" is rotated relative to the direction 36 by the quantity $\Theta_1$. Moreover, the rotation is about an axis colinear with the bounded line on which the collimator 50 is focused. FIG. 6 suggests that because of the rotation the high density element $20_D$ will not impede the illuminating radiation or will have a different effect in each of the resulting line images. As shown in FIGS. 1-3, this rotation is achieved by rotating the object 20 about an axis colinear with point 11.

In the foregoing description the object 20 is repositioned by effectively rotating it about an axis which is colinear with the bounded line. A signal sequence is derived from the radiation detecting elements 41 and 42 and stored so that there is a reference signal sequence (with the object 20 in the same position it had in the copending application) and a different signal sequence for each other position of the object 20 (per FIGS. 2 and 3).

The effect of the high density object $20_D$ is then blurred by summing all the described signal sequences to produce a sum sequence. In other words, sum sequence $\Sigma LI_i$ is produced by summing $LI_1$ with $LI_2$ and $LI_3$ ($\Sigma LI_i = LI_1 + LI_2 + LI_3$). The summation of these different signal sequences produces a line image which can be divided into two components. One component represents features along the linear element of the selected slice. This component is the same in all the sequences since the linear element remains at the line of focus in all of the positions. All other components are blurred because of the different direction of illumination. This sum sequence or sum line image may be employed without further processing. Thus a tomographic image is produced by concatenating sum line images to produce a processed tomographic image. However, the resulting image may be further improved by high frequency filtering (to be described below). The result of the processing is a filtered processed tomographic image (FTI) in which extraneous matter (the effect of features in regions other than the selected slice) such as $20_D$ have been minimized or eliminated.

Figure 8:
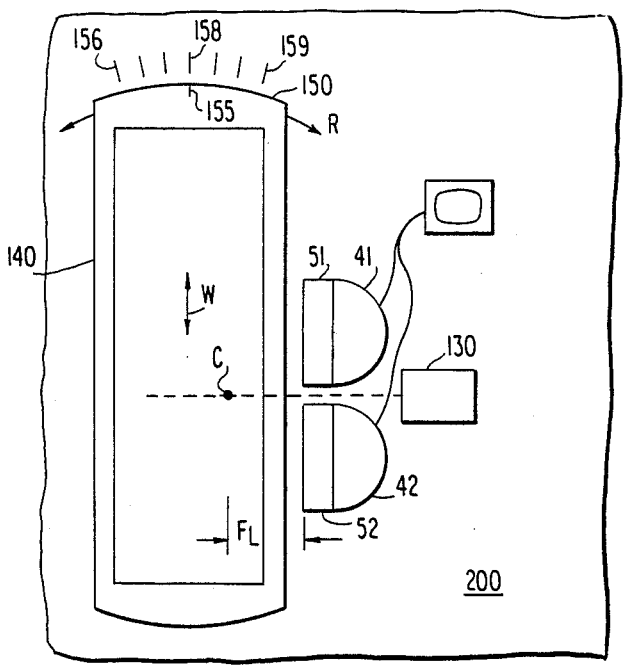
FIGS. 8 and 9 are respectively a plan view and a schematic illustration, both for the purpose of showing the apparatus and motion of the object in accordance with a first embodiment of the invention.
Figure 9:
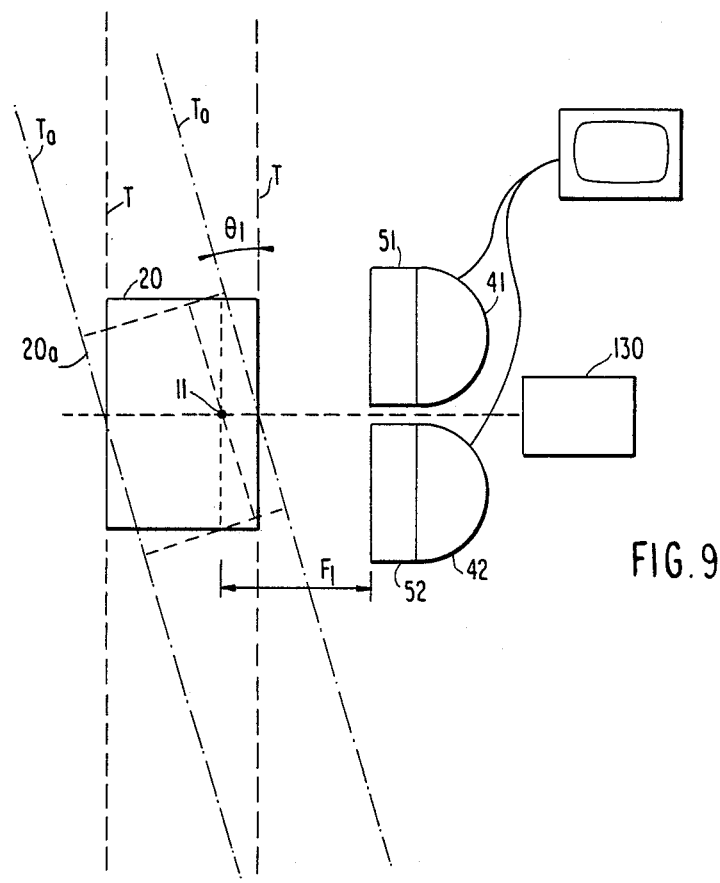

FIG. 8 shows as an example a plan view of apparatus which can be employed to produce the effect of rotating the object as required. To orient the reader, FIG. 8 shows the line collimator consisting of line collimating elements 51 and 52, the detector consisting of detector elements 41 and 42 and a display which is driven by signals from the detectors 41, 42. The x-ray source and apparatus for forming the radiation from the source into a flying pencil beam is depicted schematically at 130. This apparatus is supported on a support 200. In order to provide for the translational motion of the object to be imaged, a conveyor 140 is employed which can produce motion relative to the imaging apparatus in the direction of the arrow W. The conveyor however is not directly mounted on the support 200. Rather, the conveyor 140 is mounted on a turntable 150 which can rotate in the direction of the arrow R. For convenience the turntable 150 includes a fiducial mark 155. The turntable 150 is positioned by any conventional apparatus so that the fiducial mark 155 can be brought into coincidence with any of a plurality of corresponding marks 156-159 which are fixed with respect to the support 200. The turntable 150 is rotatable with respect to the support 200 (and therefore with respect to the imaging apparatus) about a center of rotation C. The center of rotation C lies within the sweep plane and offset from the line collimator by the focal length $F_1$. The reference character $F_1$ identifies the focal length of the line collimator 51, 52. FIG. 9 shows, in a schematic fashion, use of the turntable 150 and the effect it produces.

FIG. 9 shows the same imaging apparatus as is referred to in FIG. 8 although the turntable and other apparatus is not illustrated for convenience. The object 20, shown in full line, illustrates one position of the object 20 during the course of imaging, e.g. during a single pass. The "track" followed by the object 20 is identified by the dashed lines T. The selected slice is identified as a distance $F_1$ from the line collimator 51, 52. The bounded line, a line image of which is produced with the object 20 in the full line position, is identified in FIG. 9 by the point 11, the bounded line is of course perpendicular to the plane of the illustration, and it is the intersection between the selected slice 12 (determined by the distance $F_1$) and the sweep plane. It should be apparent how, when the object 20 is translated along the track T—T, the bounded line 11 will occupy a plurality of different, parallel and offset positions in the selected slice, so that a line image of each corresponding linear element of the slice will be produced. By using signals recorded during a single pass of the object 20 the same tomographic image will be produced as was produced by the apparatus described in the copending application. However, now with the aid of the turntable 150, the object 20 can be returned to or near its initial position, and translated again past the imaging apparatus, but at this time its track $T_a$ will be at an angle $\Theta_1$ to the track T of the object 20. The track $T_a$ is shown in FIG. 9 by the dot-dash line, and the object 20 is one position during this pass is shown by the dashed outline 20a. It should be apparent from the foregoing that the same slice 12 of the object 20 will be imaged during this pass. However, during the course of this imaging the direction of illumination will be rotated by an angle $\Theta_1$ from that illumination direction which was used in the pass of the object 20 along the track T.

It should also be apparent that by properly positioning the turntable 150, the angle between the track T and any offset track can be varied within wide limits.

Figures 10, 11, 12, 13, 14:
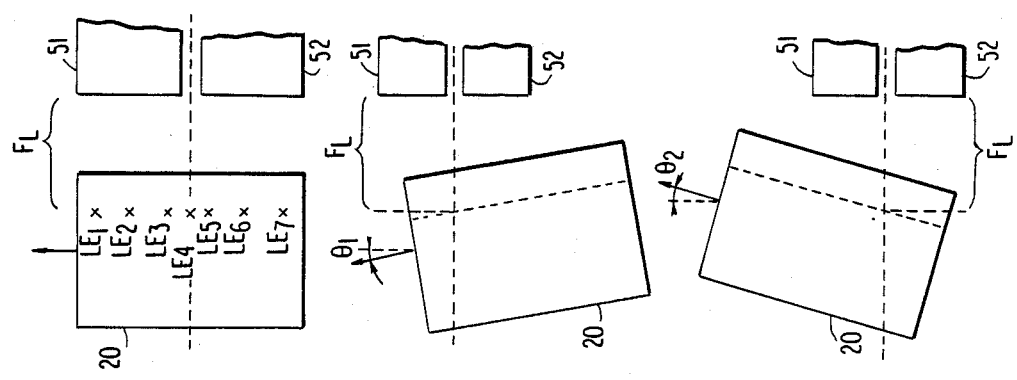
FIGS. 10, 11 and 12 relate to a first embodiment of the invention and show the motion of the object in three different directions.
FIGS. 13 and 14 illustrate data collection and storage in accordance with the first and second embodiments of the invention, respectively.

FIGS. 10-12 show schematically the object 20 passing the imaging apparatus (represented by the broken-away line collimator elements 51 and 52) so that the angle at which the selected slice is illuminated can be varied. In FIG. 10 that angle is a right angle, in FIG. 11 the angle of illumination is obtuse, and in FIG. 12 the illuminating radiation makes an acute angle with the selected slice.

For purposes of description, FIG. 10 shows the slice 12 as including line elements $LE_1$ through $LE_7$. Those skilled in the art will readily understand that many more line elements are typically used, although seven is sufficient for explanatory purposes. As the object 20 moves past the imaging apparatus in the direction shown in FIG. 10, a line image is created for each of the line elements. This is shown in FIG. 13 in the row for Pass 1, where the angle of motion is taken as 90°. A line image will be created by the swept pencil beam scanning the linear element $LE_1$, and this is represented in FIG. 13 as $LI_{11}$. A similar line image is created for each of the line elements $LE_2$ through $LE_7$, and these are represented in FIG. 13 as $LI_{12}$, $LI_{13}$, etc.

FIG. 11 shows a second pass of the object 20 where the direction of the motion of the object is now at an angle $\Theta_1$ with respect to the direction of motion in FIG. 10. During this pass (Pass 2) a line image will also be created for each of the linear elements, so that line images $LI_{21}$, $LI_{22}$, through $LI_{27}$ will be created. FIG. 12 represents a third pass at an angle $\Theta_2$. During this pass line images $LI_{n1}$, $LI_{n2}$, through $LI_{n7}$ will also be created. FIG. 13 shows that all the detected line images are stored. FIG. 13 identifies the line images as $LI_{xy}$ where x represents the pass number or angle of illumination ($1 \leq x \leq n$) and y represents or identifies the linear element of the slice ($1 \leq y \leq 7$ in this example).

The processing on groups of line images, which has already been described, requires line images of a single linear element of the slice to be processed as a group. Those line images identified in any row do not correspond to the same linear element, in fact they correspond to different linear elements. However, and referring again to FIG. 13, the line elements in any column do refer to the same linear element of the selected slice. Hence the processing for linear element $LE_1$ would proceed by summing line images $LI_{11}$, $LI_{21}$, . . . $LI_{n1}$, and summing line images $LI_{12}$, $LI_{22}$, $LI_{32}$, . . $LI_{n2}$, and so on.

FIG. 17 is useful in showing that the effective rotation does not change either the relative or even the absolute timing of receipt of the signals which are processed to produce the various line images. In FIG. 17 we illustrate schematically the object 20 in one position $20_1$ as solid lined. The reference character 36 illustrates the sweep plane (seen on edge in FIG. 17 because it is a plan view). With the object in this orientation, as it passes the imaging apparatus the time at which the illuminating beam 36 first intercepts the object is the same time at which data begins to be accumulated because of the orientation of the object 20, the location of the slice plane 12, relative to the pencil beam 36. During this pass of the object 20 it moves in the direction $W_1$. On a subsequent pass of the object 20, during which it moves in the direction $W_2$, it has been reoriented so that as the object 20 (shown in dot-dash lines) passes the imaging apparatus, the slice plane 12 coincides with the bounded line (represented by the point 11). With this orientation there is a time delay between the time the object 20 first intercepts the pencil beam 36 and the time at which the pencil beam 36 first intercepts the slice plane 12. However, because the collimator is focused on the bounded line represented by the point 11, and because the object does not intercept that point until the slice plane is again within the field of view of the collimator, the detector 41, 42 does not "see" scattered energy until the slice plane 12 reaches the bounded line 11. Therefore, relative to initial receipt of data, the line images in the two different passes are at the same relative time and no time delay is required to "align" the different line images for processing.

The foregoing has described an embodiment wherein the different positions of the object relative to the source/detector/line collimator is achieved by effectively rotating the object about an axis colinear with the bounded line. That is not, however, the only way in which different positions of the object can be achieved. Rather the object can be translated in the direction of the bounded line or parallel thereto relative to the source/detector/line collimator. This embodiment of the invention is illustrated in FIG. 7.

FIG. 7 is an elevation view schematically illustrating the components of the invention. More particularly, a source of penetrating radiant energy, an arrangement for forming therefrom a pencil beam and for sweeping that pencil beam over a line in space is represented at 130. The pencil beam 36 extends, in its sweep, between limits shown as the upper limit ray $36_U$ and lower limit ray $36_D$. The motion of the object which is described in the copending application is motion perpendicular to the plane of the illustration, such as in the direction of the arrow W. The selected slice which is being imaged is represented between the dashed lines 12. The object 20 is shown in a reference position, for example so that a reference surface of the object $20_1$ is located a distance $A_1$ from a reference surface R. With the object 20 so located, any representative point $20_P$ will be illuminated by the pencil beam 36 impinging on the point at an angle $\rho_1$ which is determined by the distance between the point $20_P$ in the slice 12 from the surface $20_1$. If the only motion of the object 20 were along the direction W, then the tomographic image produced would be the same image described in the copending application. However, in accordance with the present invention, each linear element of the slice is illuminated from a plurality of different directions. To achieve that end, the object 20 is translated along the direction of the bounded line representing the intersection between the field of view of the line collimator 51, 52 and the plane defined by the sweeping motion of the pencil beam 36, e.g. in the direction L. As the pencil beam 36 sweeps the object 20 in the position shown in FIG. 7, as has already been described the detector 41, 42 generates a signal sequence representing a line image of the slice 12. The object may now be translated in the direction L, so that for example the reference surface $20_1$ is now at a distance $A_2$ from the reference surface R. Under these circumstances and without changing the limits of the sweep ($36_U$, $36_D$), the angle at which the typical point $20_P$ is illuminated will be different from the angle in which it was illuminated before the object had been translated in the direction L. As the pencil beam 36 sweeps the object 20, a second signal sequence or line image is produced. Likewise, the object may again be translated along the direction L so that, for example, the reference surface $20_1$ now is at a distance $A_3$ from the reference surface R. As the pencil beam 36 now sweeps the object, the angle at which the typical point $20_P$ is illuminated will be different from the direction in which it had been illuminated in the two previous sweeps. The detector 41, 42 will now generate a third signal sequence or third line image.

However, rather than interrupting the motion of the object in the direction W in order to translate it along the direction of the bounded line (in the direction L), a preferred motion of the object 20 is as follows. The object 20 is first translated completely past the imaging apparatus as already described in the copending application. The support for the object 20 (such as conveyor 140) is now repositioned (by an elevator 250) such that, on a second pass of the object 20 past the imaging apparatus, the object 20 has effectively been translated in the direction L, and the process described in the copending application is repeated. Thereafter, the support for the object 20 is again translated in the direction of the arrow L and the object 20 is translated past the imaging apparatus with the object 20 at a new elevation relative to the imaging apparatus.

Figure 18:
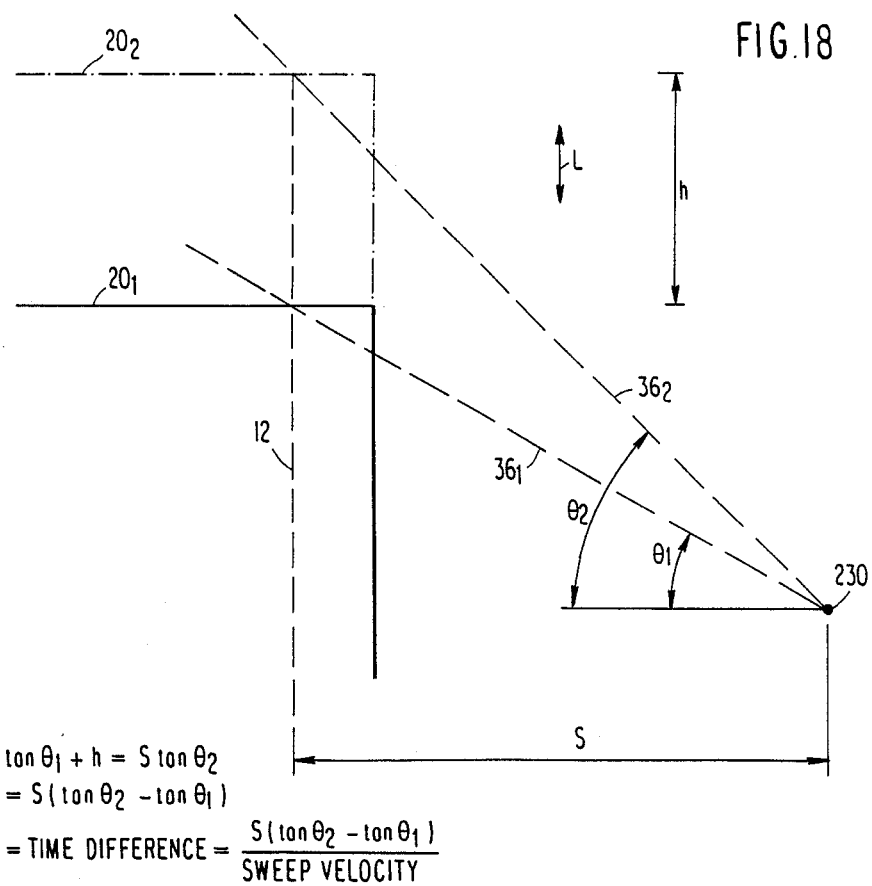
FIGS. 18 and 19 are useful in quantizing the time delay between two line images created by translating the object along the bounded line.
Figure 19:
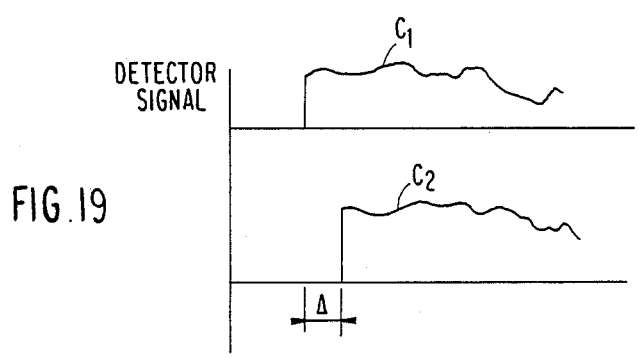

On each pass of the object 20 past the imaging apparatus, a signal sequence is recorded for each linear element of the selected slice in a fashion completely analogous to that depicted in FIGS. 10-13. Thus when the object is initially translated past the imaging apparatus at a relative height $A_1$, signal sequences such as $LI_{11}$, $LI_{12}$, $LI_{13}$, .. $LI_{17}$ are recorded. On the second pass the line images $LI_{21}$, $LI_{22}$, etc. are recorded. The processing now required is to process groups of line images related to a corresponding linear element such that for example the line images in a given column of FIG. 14 are processed as already described. However, before that processing can be employed, we must provide a relative translation (in time) between the line image created with the object in one relative position and a different line image created with the object at a different relative position. FIG. 18 is useful in explaining how that time delay is calculated. As shown in FIG. 18 the slice plane 12 is located a distance S from the effective source 230 of the pencil beam 36. With the object in one position, $20_1$ shown in full line, the pencil beam $36_1$ intercepts a given point in the slice plane 12 when the pencil beam makes an angle $\Theta_1$ with the horizontal. When the object 20 is translated in the direction L, over a distance h, the pencil beam 36 intercepts the same point in the slice plane at the angle $\Theta_2$ with the horizontal. In other words, the same point on the object is illuminated at two different points in the sweep because of the translation in the direction L. The result of this is illustrated in FIG. 19 wherein the curve $C_1$ shows the detector output for one position of the object and the curve $C_2$ shows the output of the detector for the second position of the object. It is apparent that one curve is delayed relative to another by a time difference $\Delta$. In order to properly "add" the line image represented by the curve $C_1$ to the line image represented by the curve $C_2$, we must delay $C_1$ with respect to $C_2$. The process is entirely conventional once we know the duration of the time difference $\Delta$. FIG. 18 shows how that time difference can be calculated. More particularly, with the aid of trigonometry we can write that $S \tan \Theta_1 + h = S \tan \Theta_2$. Rearranging terms, we can write that $h = S (\tan \Theta_2 - \tan \Theta_1)$. From this we can determine that the time difference $\Delta$ is the time it takes the sweep to proceed from the position $36_2$ to the position $36_1$ or vice versa. If we know what the sweep velocity is, then $\Delta$ is the ratio between $S (\tan \Theta_2 - \tan \Theta_1)$ and the sweep velocity specified in units corresponding to the unit of measure of the distance S. Thus in this embodiment we take the recorded data, and delay each of the line images vertically offset the distance h from a base or reference set by $\Delta$. We delay each line image offset by $2h$ from the reference set by $2\Delta$, etc. Once the line images are time aligned, processing is identical to that already described.

The processing used to improve the tomographic image based on illuminating the linear element from many directions is now described in detail, referring to FIG. 15.

FIG. 15 is initiated when we have created and stored all the necessary line images according to FIG. 13 or 14 and the recorded data has been time aligned, if necessary, as just described.

The first function, function F1, selects a linear element, e.g. each different column of FIGS. 13 or 14 relates to a different linear element. The next function, F2, isolates line images for the selected element, and this merely requires identifying the line images in any given column of FIG. 13 or 14. Function F3 sums isolated line images to produce the sum line image $\Sigma LI_i$, and function F4 stores that summed line image. Function F5 then determines if we have more linear element to process, e.g. have we gone through all the columns in FIG. 13 or 14. If we have not, if there are more linear elements to process, then the processing loops back to function F1 and is repeated for the next linear element. When all linear elements have been processed, we can execute function F6 to display the image from the processed line images, e.g. the processed line images are now stored and can be readily displayed.

Further processing, beyond that shown in FIG. 15, can enhance the image. This processing, shown in FIG. 16 and comprising steps F7 and F8 is performed subsequent to step F5 and prior to step F6. At the completion of step F5 we have produced a processed tomographic image, PTI. Function F7 blurs the processed tomographic image (PTI) to produce a blurred image BPTI. Function F8 then obtains the difference between BPTI and PTI to produce a filtered image FTI.

High frequency filtering of images is a conventional technique in image processing and proceeds as follows. The PTI is an image which can be considered to have two components. To the extent that the image exhibits features located within the slice being imaged, those features are sharply defined. Other features, features not located in the slice being imaged, are represented by different elements in the different line images and hence when PTI is created, these features exist as a blurred image. The purpose of high frequency filtering is to remove the blurred components. The line image of course is itself made up of a plurality of pixels. To effect high frequency filtering a kernel is selected, the kernel identifies a group of adjacent pixels. A new image (BPTI) is now created which has a pixel for each different pixel in PTI, however, each pixel in the new image (BPTI) is derived by summing a pixel and several of its adjacent pixels. For example, if we selected a kernel of three, then the nth pixel in the new image is determined by summing pixels n+1, n and n+1 from PTI. Likewise, if we had selected a kernel of five, the nth pixel in the BPTI is the sum of pixels n−2, n−1, n, n+1 and n+2 from PTI. Changing the kernel changes the extent of the filtering; a smaller kernel produces more filtering than a larger kernel. Thus the procedure produces a blurred image BPTI. The filtered image FTI is produced by subtracting the blurred image BPTI from the original image PTI. The desired tomographic image is the result. Typically the high frequency filtering is effected simultaneously in two dimensions.

It should be understood from the foregoing that the function F3 includes, for the case in which the illumination of a linear element from many different directions is implemented by translation, providing the necessary time delay to one line image relative to another which is computed as shown in FIG. 19.

It should be apparent from the foregoing that the invention achieves its objects of improving the tomographic image by illuminating a given linear element of the selected slice from many different directions, and then processing the resulting line images to "blur" and eliminate features of the line image which lie not in the slice plane 12 but between the slice plane 12 and the source of the penetrating radiation.

The examples so far described in this application encompass producing a tomographic image of a substantially planar slice. The copending application makes it clear, however, that any slice whose form is generated by a moving line can be imaged. One such slice form which has not been described so far is a cylindrical slice. It should be clear that if the different illuminating directions of the cylindrical slice are implemented by translating the object in the direction along or parallel to the bounded line, the procedures already described will suffice. The same is true where the different illuminating directions are achieved by rotating the object about an axis colinear with the bounded line. For such an object, a sequence of line images is detected and recorded (just as described in the copending application) by rotating the object about an axis parallel to but offset from the bounded line to an extent sufficient to image all of the desired slice. The object is then returned to or near its original position and it is rotated about an axis colinear with the bounded line. Thereafter the rotation of the object about the axis which is parallel to but offset from the bounded line is again performed so as to detect and record a second sequence of line images which bear a one-to-one correspondence with the sequences recorded during the first rotation with the sole difference being that the different linear elements of a slice are illuminated from a different direction as a result of the rotation of the object about the axis colinear with the bounded line. Thereafter the object is returned to or near its original position, and the object is again rotated about an axis colinear with the bounded line. Thereafter the object is again rotated about an axis parallel to but offset from the bounded line to a sufficient extent to illuminate the desired slice while at the same time detecting and recording signal sequences. This procedure is repeated a desired number of times and the different signal sequences are processed as already described.

It should also be apparent that various changes can be made to the exemplary embodiments described herein which fall within the spirit and scope of the invention which is to be construed in accordance with the attached claims.

I claimed:

1. Apparatus useful in producing a tomographic image of a selected slice of an object to be examined, said apparatus comprising:

a source of penetrating radiation, sweep means for forming energy from said source into a pencil beam and for repeatedly sweeping said pencil beam over a line in space to define a sweep plane, means for supporting said object to be examined so that said pencil beam intersects said object along a path passing through said object and said selected slice, line collimating means for filtering radiation scattered by said object, said line collimating means having a field of view which intersects said sweep plane in a bounded line so that said line collimating means passes only radiation scattered by elementary volumes of said object lying along said bounded line, positioning means for repositioning said object so that a linear segment of said selected slice of said object is illuminated by said sweeping pencil beam from a plurality of different directions, radiation detector means responsive to radiation passed by said line collimating means for generating at least a different signal sequence for each of said different directions of illumination of said linear segment of said selected slice of said object, and processing means responsive to said signal sequences for producing a line image component of a tomographic image.

2. Apparatus as recited in claim 1 wherein said processing means includes:

means for summing signal sequences for all said plurality of different directions of illumination to produce said line image component of a tomographic image.

3. Apparatus as recited in claim 1 wherein:

said positioning means includes means for rotating said object about said bounded line.

4. Apparatus as recited in claim 1 wherein:

said positioning means includes means for translating said object along said bounded line.

5. A method useful in generating a tomographic image of a selected slice of an object by generating a line image of said selected slice comprising the steps of:

providing a source of penetrating radiation, forming a pencil beam from energy emitted by said source and repeatedly sweeping said pencil beam over a line in space, supporting said object to be examined so that said pencil beam intersects said object along a path passing through said object and said selected slice, positioning said object so that a given linear segment of said selected slice of said object is illuminated from a plurality of different directions relative to said sweeping pencil beam.

filtering radiation scattered by said object to pass only radiation scattered by elementary volumes of said object lying along a line defined by a succession of intersections between said path and said selected slice by interposing a radiation absorbing structure with plural, substantially planar, radiation transmitting channels between said object and a radiation detector, detecting radiation passed by said filtering step to form a different signal sequence for each different direction from which said linear segment of said selected slice of said object is illuminated, and processing said signal sequences to form a line image component of a tomographic image.

6. A method as recited in claim 5 wherein said processing step includes:

summing signal sequences for said different directions of illumination to produce said line image component of a tomographic image.

7. A method as recited in claim 5 wherein said positioning step includes rotating said object about said defined line.

8. A method as recited in claim 5 wherein said positioning step includes translating said object along said defined line.

9. Apparatus for tomographic imaging of a selected slice of an object comprising:

detector means providing, at any time a single output signal indicative of radiation reaching all portions of said detector means, collimating means adjacent to said detector means with a field of view to pass to said detector means scattered energy originating within said field of view, a source of penetrating radiation, sweep means for forming radiation from said source into a pencil beam and for sweeping said pencil beam over a line in space so as to define a sweep plane, said sweep plane intersecting said field of view in a bounded line, means for supporting an object to be imaged so that said bounded line lies within a selected slice which is to be imaged, means for positioning said object so that a linear segment of said selected slice of said object is illuminated from a plurality of different directions by said sweeping pencil beam, storage means for storing a different signal sequence from said radiation detector means for each different direction of illumination of said linear element of said selected slice of said object, means for providing relative motion between said object and said collimating means so that, as a function of time said bounded line traces said selected slice, and image means responsive to said storage means for forming a tomographic image.

10. Apparatus as recited in claim 9 wherein said image means includes:

first processing means responsive to a group of signal sequences generated by illuminating a linear segment of said selected slice of said object from said different directions to form a line image, and second processing means for associating a group of line images to form a tomographic image.

11. Apparatus as recited in claim 10 wherein said first processing means includes:

summing means for summing signal sequences within different groups of said signal sequences to develop a sum line image for each of said groups of signal sequences, wherein a tomographic image is formed by said sum line images.

12. Apparatus as recited in claim 11 which further includes:

filtering means responsive to said tomographic image to produce a blurred tomographic image, and subtracting means to subtract said blurred tomographic image from said tomographic image to develop a filtered tomographic image.

13. Apparatus as recited in claim 12 wherein said means for positioning includes means for rotating said object about said bounded line.

14. Apparatus as recited in claim 12 wherein said means for positioning includes means for translating said object along said bounded line.

15. Apparatus as recited in claim 9 wherein said means for positioning includes means for rotating said object about said bounded line.

16. Apparatus as recited in claim 9 wherein said means for positioning includes means for translating said object along said bounded line.

* * * * *